(12) United States Patent
Singh et al.

(10) Patent No.: US 11,756,540 B2
(45) Date of Patent: Sep. 12, 2023

(54) BRAIN-INSPIRED SPOKEN LANGUAGE UNDERSTANDING SYSTEM, A DEVICE FOR IMPLEMENTING THE SYSTEM, AND METHOD OF OPERATION THEREOF

(71) Applicant: Medyug Technology Private Limited, Bangalore (IN)

(72) Inventors: Baljit Singh, Bengaluru (IN); Praveen Prakash, Bengaluru (IN)

(*) Notice: Subject to any disclaimer, the term of this patent is extended or adjusted under 35 U.S.C. 154(b) by 761 days.

(21) Appl. No.: 16/810,358

(22) Filed: Mar. 5, 2020

(65) Prior Publication Data

US 2020/0286480 A1 Sep. 10, 2020

(30) Foreign Application Priority Data

Mar. 5, 2019 (IN) .............................. 201941008481
Feb. 18, 2020 (IN) .............................. 202043006977

(51) Int. Cl.
*G10L 15/22* (2006.01)
*G10L 15/02* (2006.01)
(Continued)

(52) U.S. Cl.
CPC .............. *G10L 15/22* (2013.01); *G10L 15/02* (2013.01); *G10L 15/187* (2013.01);
(Continued)

(58) Field of Classification Search
CPC ..... G10L 15/02; G10L 15/08; G10L 15/1815; G10L 15/1822; G10L 15/187;
(Continued)

(56) References Cited

U.S. PATENT DOCUMENTS

11,227,679 B2 * 1/2022 Owen .................... G16H 10/60
2009/0216531 A1 * 8/2009 Yanagihara ............. G10L 15/30
704/235
(Continued)

*Primary Examiner* — Angela A Armstrong
(74) *Attorney, Agent, or Firm* — Nasr Patent Law LLC; Faisal K. Abou-Nasr (57) ABSTRACT

A brain-inspired spoken language understanding system, comprises: a first module that facilitates the conversion of a voice input into phoneme sequences; a buffer module that facilitates the storing of the phoneme sequences until they are clustered into a first storage as one or more meaningful thought representations; a second module that facilitates the monitoring of the reasoning, disambiguation, and prioritization of the system, in addition to controlling the system; a seventh module and an eighth module that facilitate the capturing of at least one non-verbal signal from a conversation, and create at least one time-synchronized non-verbal object, with the help of a third knowledge base; a third module that facilitates the conversion of the phoneme sequences and at least one time-synchronized non-verbal object into sequences of phonetics-based words; a fourth module that facilitates the conversion of the phonetics-based words into sequences of thought representations, with the help of a first knowledge base; a fifth module that facilitates the fine-tuning of the thought representations, with the help of the first knowledge base and a second knowledge base; and a sixth module that maintains the instance of conversation as thought representations in the form of one or more connected stories. A device for implementing the brain-inspired spoken language understanding system and its method of functioning are also disclosed.

10 Claims, 7 Drawing Sheets

(51) Int. Cl.
     *G10L 25/18*     (2013.01)
     *G10L 15/30*     (2013.01)
     *G10L 15/25*     (2013.01)
     *G10L 15/18*     (2013.01)
     *G10L 15/187*    (2013.01)

(52) U.S. Cl.
     CPC .......... *G10L 15/1815* (2013.01); *G10L 15/25* (2013.01); *G10L 15/30* (2013.01); *G10L 25/18* (2013.01); *G10L 2015/025* (2013.01); *G10L 2015/223* (2013.01)

(58) Field of Classification Search
     CPC ......... G10L 15/22; G10L 15/25; G10L 15/30; G10L 2015/025; G10L 2015/223; G10L 2015/228; G10L 25/18; G16H 10/20; G16H 10/60; G16H 15/00; G16H 40/63; Y02A 90/10
     See application file for complete search history.

(56)                References Cited

U.S. PATENT DOCUMENTS

2010/0088095 A1*  4/2010  John ................ G10L 15/22
                                                    704/235
2017/0322679 A1* 11/2017  Gordon .............. G06N 20/00

* cited by examiner

BRAIN-INSPIRED SPOKEN LANGUAGE UNDERSTANDING SYSTEM, A DEVICE FOR IMPLEMENTING THE SYSTEM, AND METHOD OF OPERATION THEREOF

CROSS REFERENCE TO EARLIER APPLICATIONS

The present disclosure is based on the Indian Patent Applications, bearing Application Numbers 201941008481, dated Mar. 5, 2019, and 202043006977, dated Feb. 18, 2020.

FIELD OF THE INVENTION

The present disclosure is generally related to a spoken and written language understanding system that is capable of understanding the non-verbal signals of a conversation, including the non-verbal signals of a speech-impaired person, to create accurate thought representations. Further, the present disclosure is also related to a device for implementing the language understanding system that helps medical practitioners, and method of operation thereof.

BACKGROUND OF THE INVENTION

There is a need for a general language understanding system, which can work like humans. Natural Language Processing (NLP) or Natural Language Understanding (NLU) are widely used technologies. However, most of the work on NLP/NLU is to get Question Answering, Topic Modeling, Semantic Parsing, Sentiment Analysis, etc. All of these use Statistical Machine Learning (ML) or Rule-Based Algorithms. There are multiple challenges with ML, as it requires large amount of data for training. However, Rule-Based Algorithms do not need training data; they are currently limited by the need for vast rules defined by human experts, and lack probabilistic computations.

The NLP or NLU are capable of understanding, and operating on human language in the raw written or spoken form only. They are not capable of utilizing non-verbal signals of conversations, including the non-verbal signs of speech-impaired persons or person with communication disorders.

An example of an industry in which language understanding systems can be implemented is the medical industry. A report from the United Nations World Health Organization states that the global healthcare workforce shortfall will reach 12.9 million by 2035. The shortage is often starkest in developing and under-developed nations. Further, rural and remote areas all over the world commonly struggle with the shortage of skilled healthcare workforce. This shortage is likely to have a considerable impact on the access of the population to healthcare.

A number of effects inevitably become evident in a health system that suffers from a shortage of skilled healthcare professionals. These include: increased workloads for the existing healthcare professionals; time constraints on physician-patient interactions; lower quality care; overworked and stressed healthcare workforce; prolonged wait time before consultations; and higher price.

'Time' plays a vital role in any health care system. If a physician spends more time with a patient, the quality of medical care will increase automatically, but he/she cannot attend to more patients, when skilled healthcare professionals are in shortage. If so, the physician has to work extra time, as a result of which his/her workload will automatically increase, leading to stress and deterioration of quality. Further, if a physician spends more time with a patient, the waiting time for other patients will go up automatically.

Since healthcare services are lifesaving services, there is no substitute to skilled healthcare professionals. Presently, there is no device or any other alternate that is available in the market globally to assist the healthcare professionals for the aforementioned purpose.

There is, therefore, a need in the art for a language understanding system which works like a human, and a device for assisting medical practitioners, which overcome the aforementioned problems and drawbacks.

SUMMARY OF THE INVENTION

A brain-inspired spoken language understanding system is disclosed. Said system comprises: a first module that facilitates the conversion of a voice input into phoneme sequences; a buffer module that facilitates the storing of the phoneme sequences until they are clustered into a first storage as one or more meaningful thought representations; and a second module that facilitates the monitoring of the reasoning, disambiguation, and prioritization of the system, in addition to controlling the system.

The brain-inspired spoken language understanding system also comprises: a seventh module and an eighth module that facilitate the capturing of at least one non-verbal signal from a conversation, and create at least one time-synchronized non-verbal object, with the help of a third knowledge base; a third module that facilitates the conversion of the phoneme sequences and the at least one time-synchronized non-verbal object into sequences of phonetics-based words; a fourth module that facilitates the conversion of the phonetics-based words into sequences of thought representations, with the help of a first knowledge base; a fifth module that facilitates the fine-tuning of the thought representations, with the help of the first knowledge base and a second knowledge base; and a sixth module that maintains the instance of conversation as thought representations in the form of one or more connected stories.

In the system, said third module, said fourth module, and said fifth module interact with each other, with the help of the second module.

The system runs the sequence possibilities throughout said third module, said fourth module, and said fifth module like a pipeline, with feedback coming from forward modules to prior modules.

A device for implementing the brain-inspired spoken language understanding system comprises: at least one central processing unit that is in communication with at least one memory where at least one module of the brain-inspired spoken language understanding system resides; one or more communication units, which facilitate the connecting of the device with one or more health care devices, and the connecting of the device with a network to transmit or store the output; at least one input unit; a display unit that presents the output to the user; at least one microphone that facilitates the capturing of a voice of the user; at least one speaker that facilitates the delivering of an audio output to the user; at least one camera that facilitates the capturing of images/videos of the user for lip-reading and gesture identification; and one or more supplementary processing units with at least one memory and one or more communication units to support the at least one central processing unit in handling a plurality of tasks.

DESCRIPTION OF THE INVENTION

Throughout this specification, the use of the word "comprise" and "include", and variations such as "comprises", "comprising", "includes", and "including" may imply the inclusion of an element or elements not specifically recited.

Throughout the specification, the use of the phrase 'health workforce' or 'health care professionals', and variations thereof may include medical practitioners, physicians, doctors, etc.

Throughout the specification, the use of the phrase "non-verbal signal" and variations thereof may include any non-verbal signals from a conversation with a person. The person may be either a normal person or a speech-impaired person. The speech-impaired person includes a person with communication disorder.

Throughout the specification, the use of the phrase 'thought representation' and its variations are used in the meaning of a language-independent representation of human thoughts.

Throughout the specification, the word 'phoneme' and its variations are used in the meaning of any of the perceptually distinct units of sound in a specified language that form specific words in the language. The examples in this disclosure are taken from the IPA (International Phonetic Alphabets), but these are only for the purposes of representation, and the system can use any other phonetic standards.

Throughout the specification, the phrase 'phonetics-based word', 'phonetics-based words', 'spoken word', 'spoken words', 'PBW', and their variations are used to denote spoken language words, regardless of spelling. For example "there" and "their" are examples of single phonetics-based words which are spelt differently, but have the same phonetics. The representation of PBW is based on language-independent phonemes and may be inspired by the IPA (International Phonetic Alphabets) standards, but may also use other language-independent phonetic standards.

Throughout the specification, the phrase 'entities or concepts' and its variations are used to denote concepts, which represent an object or action (physical, behavioral, or mental), performed by these objects. For example "Diabetes" is a concept and "Running" is another concept.

Throughout the specification, the phrases 'speech-impaired person', 'person with communication disorder', and their variations are used interchangeably with the same meaning.

Throughout this specification, the phrases "at least one" and "one or more" are used interchangeably.

Figure 1:
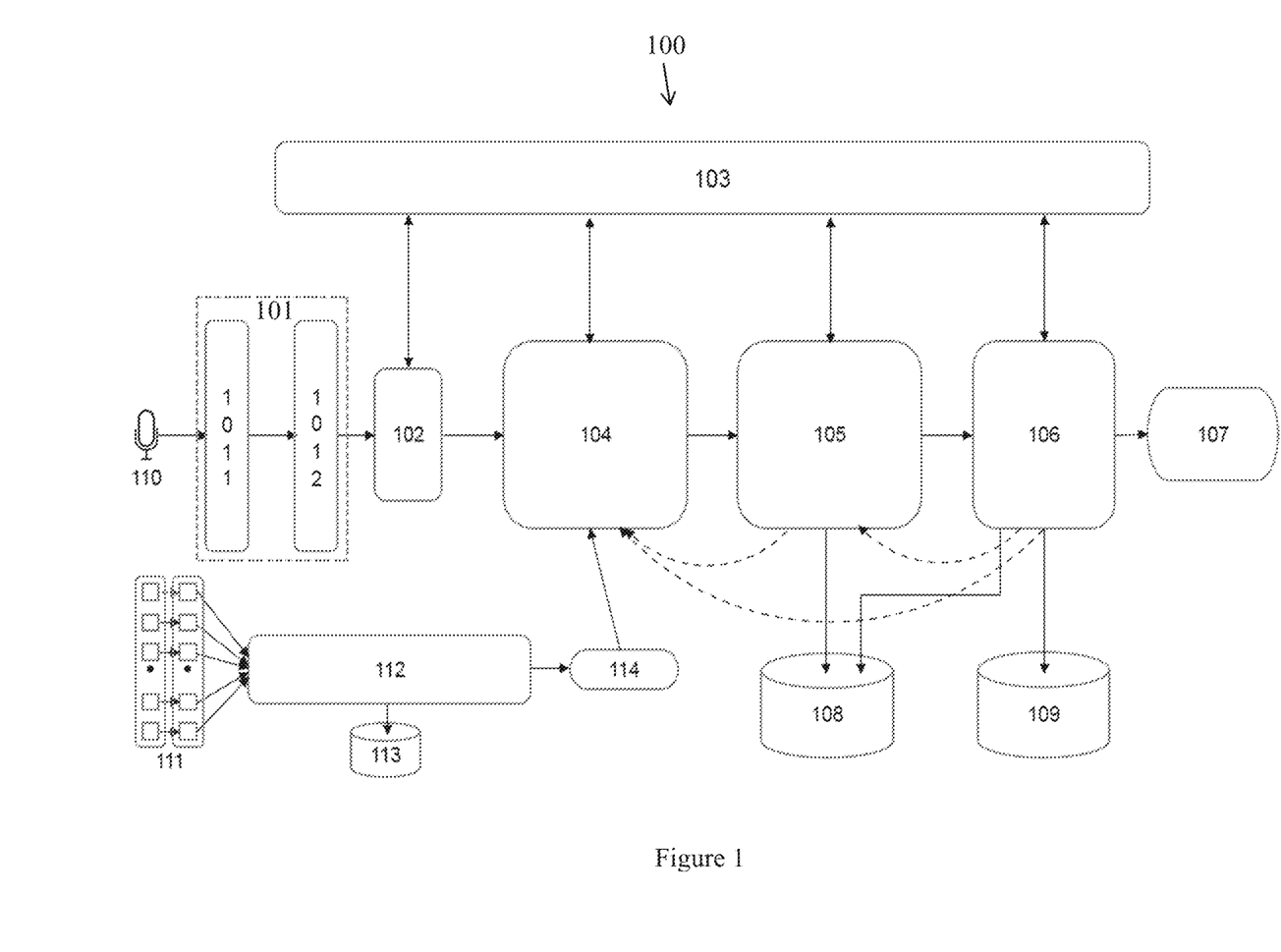
FIG. 1 illustrates an embodiment of a brain-inspired spoken language understanding system, in accordance with the present disclosure.

A brain-inspired spoken language understanding system (BISLU; 100) is disclosed. As illustrated in FIG. 1, the BISLU system (100) comprises: a first module (101) that facilitates the conversion of a voice input received through one or more microphones (110) into phoneme sequences, said first module (101) comprising: a first unit (1011) that converts the voice input received into spectrograms, and a second unit (1012) that converts the spectrograms into phonemes with pause time between them, if applicable; a buffer module (102) that facilitates the storing of the phoneme sequences until they are clustered into a first storage as one or more meaningful thought representations; a second module (103) that facilitates the monitoring of the reasoning, disambiguation, and prioritization of the system (100), in addition to controlling the system (100); a seventh module (111) that comprises: at least one sensor that captures at least one non-verbal signal from a conversation, and a pre-processing unit that facilitates the pre-processing of the at least one non-verbal signal received from the at least one sensor; an eighth module (112) that is configured to classify and transform the at least one non-verbal signal received from the seventh module (111) into at least one symbol, and creates at least one time-synchronized non-verbal object by permuting and matching the at least one symbol against a third knowledge base (113); a ninth module (114) that facilitates the transmission of the at least one object received from the eighth module (112), along with time-stamp to a third module (104), said third module (104) facilitating the conversion of the phoneme sequences and at least one time-synchronized non-verbal object into sequences of phonetics-based words; a fourth module (105) that facilitates the conversion of the phonetics-based words into sequences of thought representations, with the help of a first knowledge base (108), which may be based on the Unified Medical Language System (UMLS); a fifth module (106) that facilitates the fine-tuning of the thought representations received from the fourth module (105) by: merging two or more thought representations, inferring new thought representations, correcting the thought representations, and/or filling one or more missing information in the thought representations, with the help of the first knowledge base (108) and a second knowledge base (109); and a sixth module (107) that maintains the instance of conversation as thought representations in the form of one or more connected stories as thought cloud, with said third module (104), said fourth module (105), and said fifth module (106) interacting with each other, with the help of the second module (103).

In an embodiment of the present disclosure, the pre-processing is a low-latency signal-processing operation performed in a hardware in analog or digital domain, and optionally with the help of a software, if the pre-processing in digital domain. The pre-processing includes, but is not limited to, operations such as amplification, attenuation, noise-removal, filtering, beamforming, etc.

In another embodiment of the present disclosure, the third module (104) may use non-verbal objects of lip-reading from a camera input (from the seventh module (111)) to disambiguate the phonetics of an alphabet being processed.

For example, the conversion of voice input into phoneme sequences in the first module (101) happens as follows: time-based discrete samples of voice sampled at a particular frequency are converted from time domain signals to frequency domain signals known as spectrograms. These spectrograms are then converted into sequences of phonemes, such as "p", "b", "β", etc., using either Artificial Neural Network (ANN) or Statistical Machine Learning (ML) techniques.

In another example, the conversion of the phoneme sequences into sequences of phonetics-based words in the third module (104) happens as follows: for an English utterance of the phrase "test done", a phoneme sequence of (t, ε, s, t, <pause>, d, ∧, n) leads to a phonetic based word (PBW) as ("tεst", "d∧n").

In yet another example, the conversion of the phonetics-based words into sequences of thought representations in the fourth module (105) happens as follows: let us assume a simple sentence, which is uttered by a speaker as "I have got test done." The phoneme sequence for these would be (a,ɪ, h,æ,v, g, ɒ ,t, t,ε,s,t, d,∧,n). A pause is represented by a space for simplicity. However, pauses may or may not be there in a real-word scenario. This is converted to a phonetics-based word (PBW) sequence as (aɪ, hæv, g ɒ t, tεst, d∧m). This sequence of PBWs is treated as a unique thought representation (TR), which clearly specifies a thought as Person-GotTest ("Initiator as First Person", "Beneficiary Person as First person", "Test Name as Generic Class Pointer", Inflections ("Temporal Sense as Past", "Possibility as Confirmed", . . . ), . . . ). This is a simple English representation of a TR. However, the system representation may take any other suitable formats.

A story is formed by: merging two or more thought representations, inferring new thought representations, correcting the thought representations, and/or filling one or more missing information in the thought representations in the fifth module (106). This can be understood from the below example. Let us say a patient mentions these two sentences in the same conversation, but separated by many other sentences. "I am having trouble with my head", and "The pain is unbearable." These could imply that the patient is specifically mentioning about a headache and the actual thought would be "I am having a headache." Similar thoughts uttered by the patient, which are strongly or loosely connected in time, form multiple independent sequences of thoughts, leading to stories.

In an embodiment of the present disclosure, the BISLU system (100) follows spoken language principles. The system (100) takes sequences of phonemes with time gaps between them. These sequences of phonemes are sequentially accumulated to form thoughts, which may or may not be connecting each other.

The non-verbal signals are processed into at least one time-synchronized non-verbal object that aids in the process of thought construction from phonetics-based words.

A non-verbal signal can be, for example, multiple video streams from multiple cameras. The video data maybe fed into an Artificial Neural Network (ANN) to identify symbolic information, such as a face that identifies a person and his/her body parts—for example a finger pointing to abdomen. The symbolic information is processed to create an "object", which is a more complex composition of symbolic elements into a concept, for example, "the doctor feeling the patient's knee-cap." Together with an utterance such as "does it hurt here when I press it", the non-verbal information helps construct a complete and accurate thought representation (TR) that the doctor is asking about the patient's knee.

In another embodiment of the present disclosure, the second module (103) also acts as a master controller for the buffer module (102), the third module (104), the fourth module (105), and the fifth module (106). All the reasoning, prioritization, and disambiguation done by the second module (103) is reflected in the third module (104), the fourth module (105), and the fifth module (106).

In yet another embodiment of the present disclosure, the first knowledge base (108) may be based on Unified Medical Language System (UMLS) and comprises all the words/vocabularies/lingo related to clinical concepts and limited worldly knowledge concepts. The first knowledge base (108) comprises both language-independent and language-dependent portions. For example, the concept "diabetes" and its relations with other concepts are language-independent, but the actual phonetics-based words or spellings are different in different languages and, hence, are language dependent.

In yet another embodiment of the present disclosure, the at least one sensor in the seventh module (111) includes, but is not limited to, at least one camera, at least one ECG sensor, at least one heart beat sensor, at least one odour sensor, at least one MRI sensor, and the like.

In yet another embodiment of the present disclosure, the at least one non-verbal signal includes, but is not limited to, background sounds or noise from multiple microphones, visual signals, like an image or a document being referred to in a conversation, images and/or videos from camera, odor detection systems, indicating presence of a chemical signature in the environment, ECG, heart rate, and functional MRI images. Further, the non-verbal signals may also be presented through other forms in the sound itself, such as intonation and change in pitch or rate.

In yet another embodiment of the present disclosure, the pre-processing of the at least one non-verbal signal received from the at least one sensor may be performed either in the integrated pre-processing unit or an external pre-processing unit over a network.

In yet another embodiment of the present disclosure, the classification and transformation of the at least one non-verbal signal received from the seventh module (111) into at least one symbol is performed using at least one Artificial Neural Network (ANN).

The first knowledge base (108) comprises two graphs. The first is a semantic graph, which shows classes or semantic types of concepts, and their relation to each other. For example, classes such as disease, symptom, etc., are specified in this graph as types of entities or concepts, and how they are related to each other. The second graph comprises actual names of diseases, such as "diabetes type 2", "dengue fever", etc., and how these concepts are related to each other. Each concept in the second graph also comprises other attributes, such as semantic type, definitions, etc. The first knowledge base (108), in general, comprises all types of named entities, properties defining these named entities, as well as the possible actions related to these named entities. However, the first knowledge base (108) is not limited to the two graphs only, which can be merged, or more graphs may be added to represent entities in the real-world.

In yet another embodiment of the present disclosure, the second knowledge base (109) comprises a thought representation semantic network, which has different types of thought representation hierarchy from broader thoughts at the top to specific thoughts at the bottom of hierarchy. The second knowledge base (109) is language-independent. The second knowledge base (109) also comprises two graphs like the first knowledge base (108). However, the knowledge and relations are on a thought-level unlike entity level in the first knowledge base (108). The first graph shows semantic network of thoughts, where multiple types of thoughts are hierarchically connected. For example, it may comprise a class of thoughts as "Person-Possess-Symptom". The second graph comprises the instances of these types of thoughts and information about how they are related to each other.

The third knowledge base (113) provides a look-up for non-verbal symbols into known complex objects. These objects provide a concept-name to concurrently occurring symbols at a higher level of abstraction. The objects from this third knowledge base (113) participate in further processing: in the third module (104), in the fourth module (105), and in the fifth module (106)

In yet another embodiment of the present disclosure, the first knowledge base (108), the second knowledge base (109), and the third knowledge base (113) are suitably created or modified to make the system (100) suitable for any domain or industry other than the healthcare/medical domain/industry.

In yet another embodiment of the present disclosure, the system (100) runs the sequence possibilities throughout said third module (104), said fourth module (105), and said fifth module (106) like a pipeline with feedback coming from forward modules to prior modules (106 to 105, 106 to 104, and 105 to 104). The system (100) ensures that the first output coming out from the system (100) is appropriate. However, the second module (103) can always direct said third module (104), said fourth module (105), and said fifth module (106) to evaluate other possibilities too.

For example, let us consider the sequence of phonemes (a,ɪ,w,ɪ,l,s,w,ɪ,m, t,u; b,æ,η,k), which correspond to the sentence "I will swim to bank." Let us just evaluate the possible meanings of "bank". The BISLU system (100) evaluates the possibilities in sequence. First, it takes the first possibility ("river bank") in the third module (104) and pushes it through the fourth module (105) and the fifth module (106). While the fourth module (105) and the fifth module (106) are evaluating the first possibility, the third module (104), at the same time, looks at a second possibility ("financial institution"). Eventually, the third module (104) gets feedback from the second module (103) to terminate the evaluation of other possibilities and that first possibility was a success. The first possibility is picked up looking at the context in the same sentence or previous sentences to ensure that it picks the best option first to save time and power. This also ensures lesser hardware is required for computation, thus saving costs.

In yet another embodiment of the present disclosure, the first knowledge base (108) and the second knowledge base (109) are configured to have prioritized access based on frequency and recentness of access. This helps in prioritizing frequent and recent items to be evaluated first, enabling the system (100) to have a faster response time.

Figure 2:
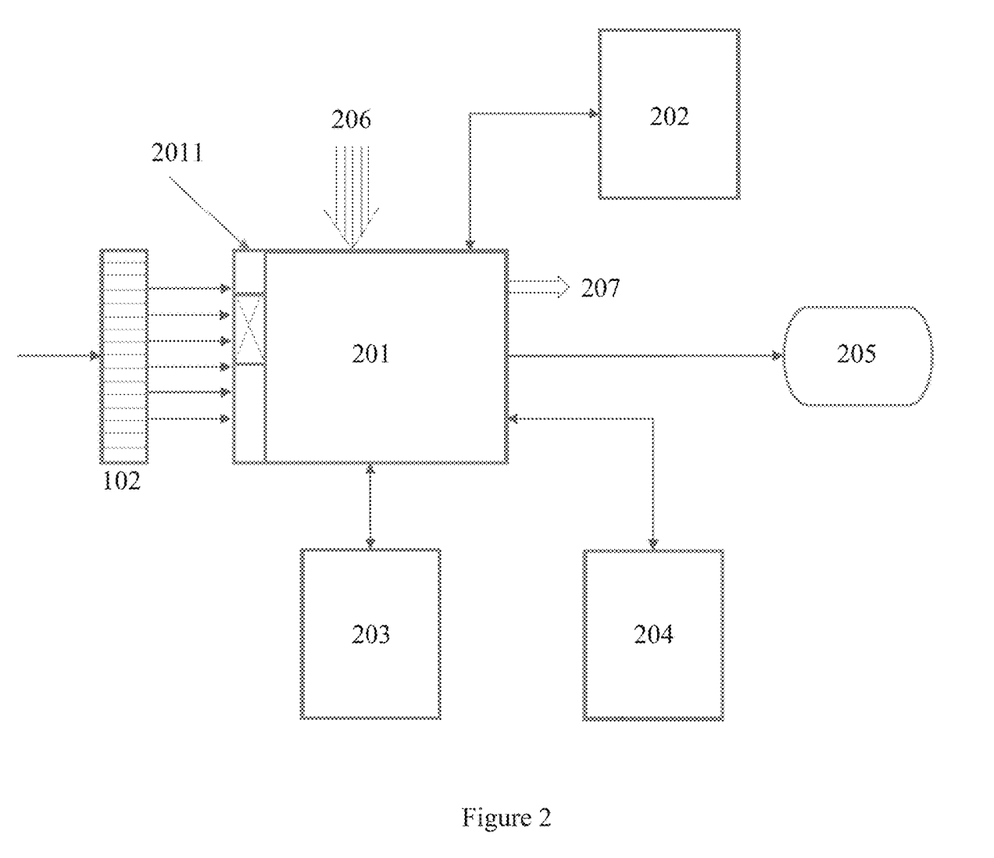
FIG. 2 illustrates an embodiment of a third module of the brain-inspired spoken language understanding system, in accordance with the present disclosure.

As illustrated in FIG. 2, the third module (104) comprises: a third unit (201) that collects phonemes from the buffer module (102) and uses sliding dynamic width window technique (2011) over these phonemes to create a sequence of best possible phonetics-based words (205), said third unit (201) receiving one or more feedback (206) from the other modules (105, 106) through the second module (103) to decide whether the phonetics-based words (205) are meaningful or not, and sending status signals (207) to the second module (103) after the completion of a task; a fourth unit (202) that receives the phoneme sequences from the third unit (201) and converts them into phonetics-based words; a fifth unit (203) that receives the sequence of phonetics-based words identified by the third unit (201) and refines the phonetics-based words; and a sixth unit (204), which is a phoneme similarity matrix that resolves conflicting words by using similar sounding phonemes. There are many phonemes which sound similar. Let us say "b" or "d". The similarity matrix comprises information on which phonemes are similar to each other and, hence, helps the third unit (201) to interchange between similar sounding phonemes to check the best possible word for a meaningful thought representation.

The sliding dynamic width window technique can be illustrated with the following example. It is technique where, for a bigger data length, of say 10, a smaller window, of say 3, is taken and is slid from the beginning to end to pick only a part of data for processing. In this case, the phoneme sequence is larger for a sentence and it will be smaller for words. Let us say the system (100) has a phoneme sequence of "My Kart is full." In this case, while moving, the taken phoneme sequence of "Kar" could match to "car", but when the window is increased further to check if a better word can be taken, "Kart" is obtained as a better word match. The window is sliding as well as of variable width. The reason for doing this is that the window can even go back to previously picked words to better match new words for getting a meaningful thought.

In an embodiment of the present disclosure, the third unit (201) is language-independent and interacts with the other modules (105, 106) and the other units (202, 203, 204), either sequentially or in parallel, to identify the sequence of best possible phonetics-based words (205).

In another embodiment of the present disclosure, the fourth unit (202) is language-dependent and runs as an independent task in parallel with the rest.

In yet another embodiment of the present disclosure, the fifth unit (203) is language-dependent and runs as an independent task in parallel with the rest.

In yet another embodiment of the present disclosure, the sixth unit (204) is language-independent and runs as an independent task in parallel with the rest.

Figure 3:
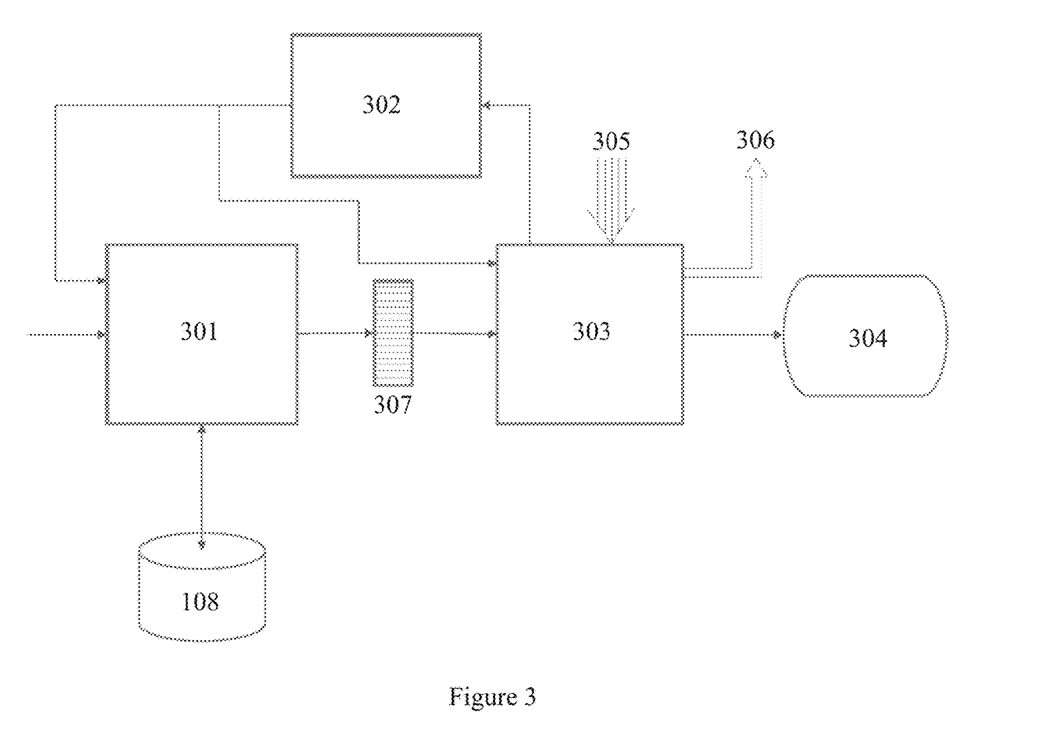
FIG. 3 illustrates an embodiment of a fourth module of the brain-inspired spoken language understanding system, in accordance with the present disclosure.

As illustrated in FIG. 3, the fourth module (105) comprises: a seventh unit (301) that takes a sequence of phonetics-based words as input, and, while looking at expected output from an eighth unit (302), the seventh unit (301) fetches possible concepts/entities from a single phonetics-based word or a group of phonetics-based words, with the help of the first knowledge base (108), and sends the output concepts to an entity possibility buffer unit (307); the eighth unit (302) that holds sequences of phonetics-based words since the last completion of a thought representation and outputs: next expected phonetics-based words or concept type for the given sequence of previous phonetic-based words, and thought representation for sequence of phonetic-based words; and a ninth unit (303) that facilitates the identification of the best possible and meaningful thought representations (304) by reasoning the phonetics-based words in the entity possibility buffer unit (307) with all the thought representations obtained since the last completed thought representation process, said ninth unit (303) receiving one or more feedback (305) from the other modules (106) through the second module (103) to decide whether the thought representations (304) are meaningful or not, and sending a status signal (306) to the second module (103) during the current task or after completion of the task.

In an embodiment of the present disclosure, the seventh unit (301) is language-independent and interacts with the other units (302, 303) in parallel to identify the sequence of best possible thought representations (304).

In another embodiment of the present disclosure, the eighth unit (302) is language-dependent and runs as an independent task in parallel with the rest.

In yet another embodiment of the present disclosure, the ninth unit (303) is language-independent and runs on the same process as the second module (103).

In yet another embodiment of the present disclosure, the first knowledge base (108) is either language-independent or language-dependent.

Figure 4:
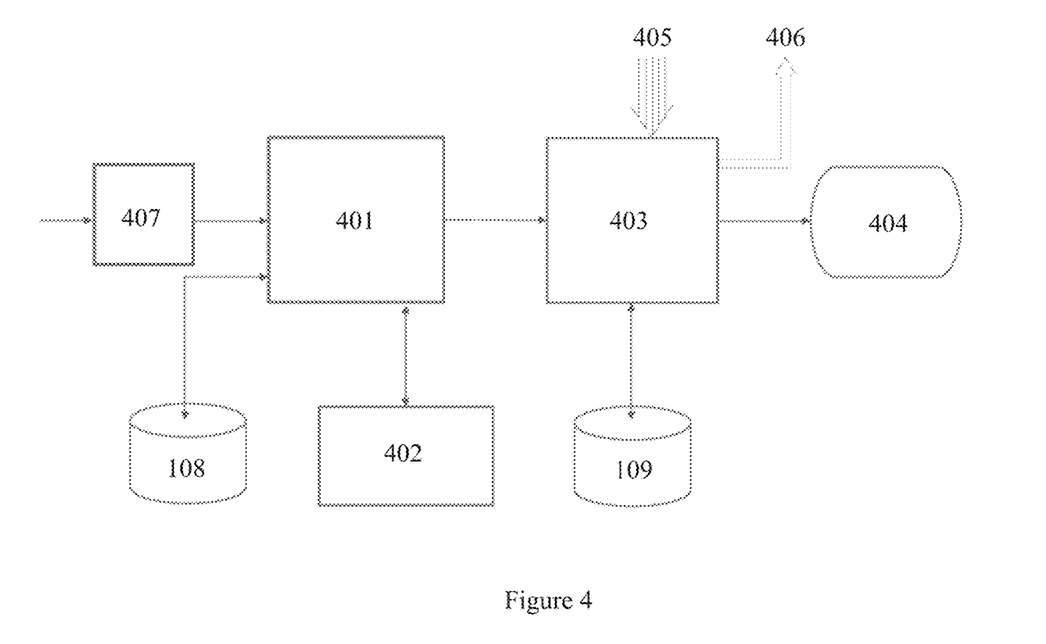
FIG. 4 illustrates an embodiment of a fifth module of the brain-inspired spoken language understanding system, in accordance with the present disclosure.

As illustrated in FIG. 4, the fifth module (106) comprises: an entity de-referencing (EDR) unit (407) that receives the incoming thought representation sequences from the fourth module (105), keeps track of all the entities mentioned throughout the conversation, and updates the incoming thought representation sequences with well-specified entities; a tenth unit (401) that checks whether the thought representations are well-connected and switching between their contexts is meaningful, with the help of the first knowledge base (108) and an eleventh unit (402) that explores all possible thought representation context connectivity; and a twelfth unit (403) that facilitates the fine-tuning of the thought representations received from the fourth module (105) by: merging two or more thought representations, inferring new thought representations, correcting the thought representations, and/or filling one or more missing information in previous thought representations, with the help of the second knowledge base (109), thereby creating a story as a thought cloud around the thought representation sequence (404), said twelfth unit (403) receiving one or more feedback (405) from the second module (103) to decide whether to process further or stop processing, and sending a status signal (406) to the second module (103) during the current task or after the completion of the task.

In an embodiment of the present disclosure, the fifth module (106) is augmented, with the help of the EDR unit (407). Said EDR unit (407) keeps track of all the entities mentioned throughout the conversation and updates the incoming thought representation sequences with well-specified entities for further processing within the fifth module (106). Here, the entity maybe referred directly by its name (e.g. "the Toyota Corolla"), by a pronoun (e.g. "it"), by a common-noun (e.g. "the car"), by its quality (e.g. "the red one"), with registration number (e.g. "XYZ"), by deeper knowledge-based logical inference (e.g. "my set of wheels", which can be translated as "the car I drive"), or by non-verbal means (e.g. a gesture with finger pointing and saying "that car"). The deeper knowledge-based references and verbal references are both resolved in the TR domain; if a resolution is not reached, a resolution is tried with the non-verbal objects from the ninth module (114). The EDR unit (407) is also associated with 404 for referring to the earlier thought representation. Thus, the EDR unit (407) helps in accurate processing of the thought representation with fewer ambiguities remaining.

In another embodiment of the present disclosure, the tenth unit (401) acts as an anomaly detection unit. The tenth unit (401) detects two types of anomalies. First is context-switching specific and other one is thought-specific. When a speaker talks, there is a pattern in context switching. Context here would mean what a person broadly is talking about. For example let us say a person is talking about his medical condition. He would stay within that context until he is almost done. If the person talks ten sentences each on his medical condition, he may switch context very few times, but would not switch context after each sentence. The exact pattern in context switching is learned over time and is dependent on the domain of conversation. This learned pattern is stored in the eleventh unit (402). The second type of anomaly is specific to a thought. Let us take a sentence "I have diabetes and value is 102". Here, if 102 is taken as "temperature" then it is flagged as an anomaly and is dropped. However, 102, as sugar level is not an anomaly. This is determined by the first knowledge base (108), where such relations are stored between sugar level and diabetes, but not between temperature and diabetes.

In yet another embodiment of the present disclosure, the tenth unit (401) is language-independent and interacts with the other units (108, 402, and 403) in parallel to identify whether the thought representations are well-connected and switching between their contexts is meaningful. The tenth unit (401) runs as an independent task in parallel with the rest.

In another embodiment of the present disclosure, the eleventh unit (402) is language-independent and interacts with the other units (401) in parallel to identify whether the thought representations are well-connected and switching between their contexts is meaningful.

In yet another embodiment of the present disclosure, the twelfth unit (403) is language-independent and runs as an independent task in parallel with the rest.

In yet another embodiment of the present disclosure, the fourth unit (202) in the third module (104), the eighth unit (302) in the fourth module (105), and the eleventh unit (402) in the fifth module (106) are configured as a predictive memories. These memories facilitate the identification of the possibilities of outputs for a given sequence of inputs.

In yet another embodiment of the present disclosure, the fourth unit (202), the fifth unit (203), the eighth unit (302), and the eleventh unit (402) are suitably modified to make the system (100) suitable for any domain other than healthcare/medical domain.

Figure 5:
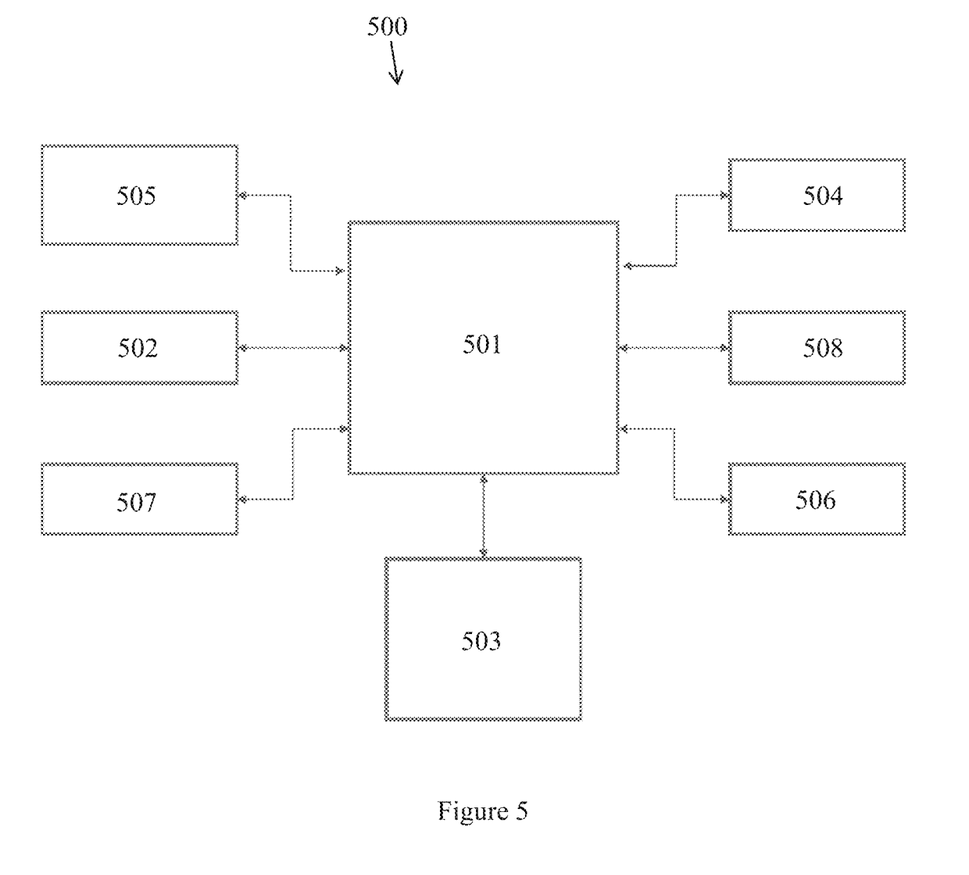
FIG. 5 illustrates an embodiment of a device in which the brain-inspired spoken language understanding system is implemented, in accordance with the present disclosure.

A device (500) for implementing the BISLU system (100) is illustrated in FIG. 5. The device (500) is a brain-inspired natural conversation understanding device, which works prior to and during a consultation of a patient with a doctor, and acts as an assistant to the doctor. The device listens to the patient and/or doctor conversation, and creates an internal representation of their conversation. The internal representation is then used to create a patient summary by summarizing patient complaints and history. The internal representation is also used to create an automatic entry into an external Electronic Medical Records System/Hospital Management System.

The device (500), as illustrated in FIG. 5, comprises at least one central processing unit (501), said central processing unit (501) being in communication with at least one memory, where at least one module of the BISLU system (100) resides; one or more communication units, which facilitate the connecting of the device (500) with one or more health care devices (503), to collect the relevant data from a user, and/or with a network (503), such as the cloud to transmit or store the output; at least one input unit (502); a display unit (504) that presents the output to the user; at least one microphone (505) that captures a voice of the user; at least one speaker (506) that delivers an audio output to the user; at least one camera (507) that captures images/videos of the user for lip-reading and gesture identification; and one or more supplementary processing units (508) with at least one memory and one or more communication units to support the central processing unit (501) in handling a plurality of tasks.

In an embodiment of the present disclosure, the one or more health care devices include, but are not limited to, one or more of: digital BP, digital Pulse Oximetry, digital Stethoscope, digital Weighing device, digital Height measuring device, digital Thermometer, ECG, digital Glucometer, or the like.

In another embodiment of the present disclosure, the one or more communication units in the central processing units (501, 508) support any wired or wireless communication technology known in the art, including, but not limited to, Ethernet, Bluetooth Low Energy, Bluetooth, Near-Field Communication, or the like.

In yet another embodiment of the present disclosure, the at least one input unit (502) includes, but is not limited to, keyboard, mouse, or the like.

In yet another embodiment of the present disclosure, the at least one memory in the central processing units (501, 508) includes any suitable volatile or non-volatile computer-readable storage media.

In yet another embodiment of the present disclosure, the device (500) communicates with the other systems, such as hospital management system or electronic medical record system, for sharing its results.

In yet another embodiment of the present disclosure, the device (500) in which the BISLU system (100) is implemented may work on a networked environment. The network may be the Internet, a virtual private network, a local area network, a wide area network, a broadband digital network, or any other appropriate structure for enabling communication between two or more nodes or locations. The network may include a shared, public, or private data network. Further, the network may encompass a wide area or local area, and may include one or more wired and/or wireless connections.

The working of the device (500) in which the BISLU system (100) is implemented shall now be explained.

Figure 6:
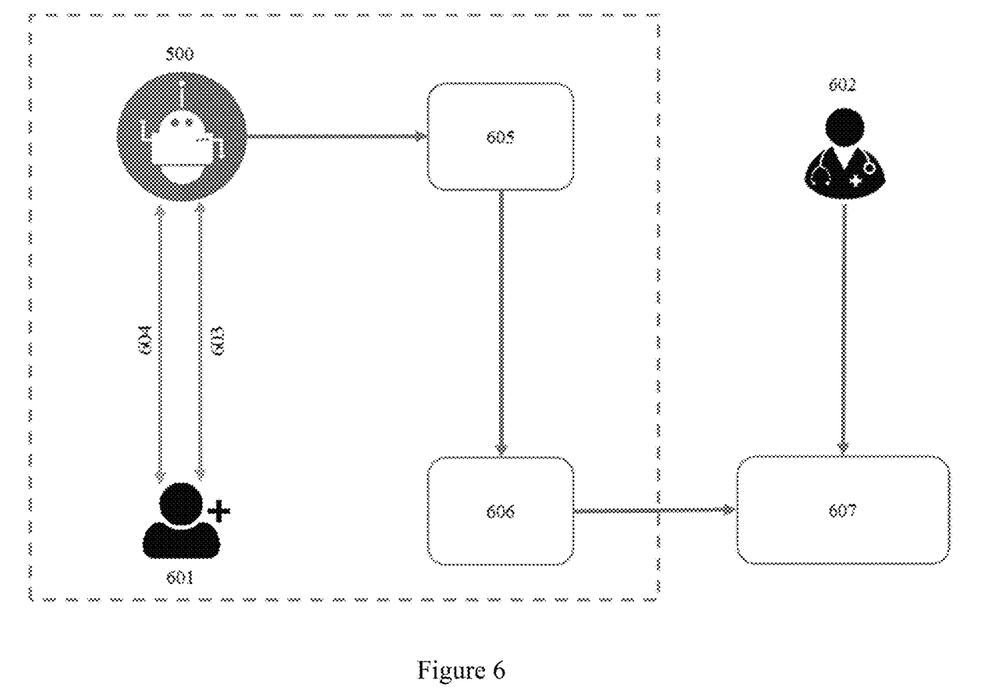
FIG. 6 illustrates an embodiment of the steps involved during the pre-consultation of the device with the patient, in accordance with the present disclosure.

While a patient (601) is at a hospital for consulting with a doctor (602), the patient (601) has a pre-consultation with the device (500). As illustrated in FIG. 6, this comprises:

1. Listening (603) to the complaints explained by the patient (601) or his/her caretaker. The device (500) may also communicate with the patient (601) via voice. Here, the patient (601) walks into a room where the device (500) is present. The room may have a human clinician like a Nurse. The device (500) starts a conversation with the patient (601) and encourages the patient to talk about his/her health issues, medical history, and complaints. The device (500) may ask questions to the patient for clarifying certain confusions it may have. These questions can be voice-based or may be displayed on the display unit (504).
2. Understanding the complaints, with the help of the BISLU system (100). While the device (500) is listening to the patient, it processes the voice using the BISLU system (100) and creates thought representations.
3. Using the at least one camera to identify certain phonemes (603) from the patient's or caretaker's gestures and lip movements. The device (500) uses the at least one camera to read the lip of the patient or the caretaker and differentiate between similarly sounding phonemes like "p" and "b". Similarly, it also identifies gestures, like hand movement or facial expressions, to enhance its understanding. For example a patient may make certain facial expressions, which reflect the gravity of pain. Further, the patient may use his/her hand to pinpoint the location of pain by uttering sentences like "I have pain here." The "here" in this line refers to the location that is pointed to by the patient, which is picked up by the device (500) to dereference the word. The same at least one camera may also be used to read displayed entries on healthcare devices like weight, BP, etc.
4. Clarifying certain sentences or utterances made by the patient or his/her caretaker to disambiguate.
5. Asking questions for further understanding of the patient's medical condition/problem. Based on the patient's condition, the device (500) may also ask further questions like a doctor to know more about the patient's medical condition. For example, if the patient indicates he/she had fever of 102, the device (500) may ask if the patient had headache along with fever.
6. Collecting one or more clinical vital data (604) of the patient, such as temperature, BP, weight, height, sugar level, ECG, etc., with the help of the relevant health care devices connected with the device (500), depending on the patient's medical problem or specific to the preferences of the doctor (602).
7. Preparing a summary (605) of the discussion with information, such as patient's current complaints, along with patient's medical/family history.
8. Presenting the summary to the patient (601) for his/her verification and making corrections (606) as requested by the patient (601).
9. And, preparing a doctor-specific summary and forwarding the summary (607) to a doctor (602) for his/her review. This helps the doctor save time, as the doctor is presented with a concise and quick summary of the patient's condition. This also improves the accuracy, as all the conditions of the patient are recorded by the device (500). This ensures no conditions are left out, and all the medical conditions are verified and corrected by the patient.

However, the pre-consultation with the device (500) may not follow the exact sequence as explained above. The sequences may vary on a case-to-case basis and/or with respect to situations.

Figure 7:
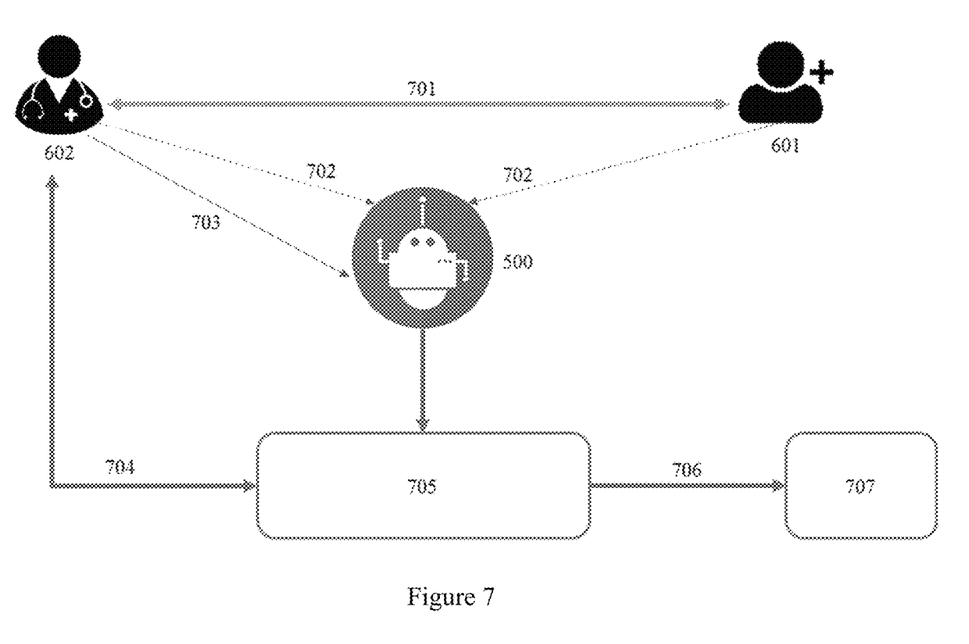
FIG. 7 illustrates an embodiment of the steps involved in the passive participation process of the device during doctor-patient consultation, in accordance with the present disclosure.

When the patient (601) is in consultation (701) with the doctor (602), the device (500) plays a passive role and listens actively to both the doctor (602) and the patient (601). As illustrated in FIG. 7, the passive listening process of the device (500) comprises:

1. Listening to the conversation (702) between the doctor (602) and the patient (601) or his/her caretaker. If allowed by the doctor (602), the device (500) may also interact in a limited manner.
2. Understanding the conversation, with the help of the BISLU system (100). The device (500) continuously listens to the doctor (602) and the patient (601). The BISLU system (100) understands the conversation and creates thought representations of the conversation.
3. Modifying the patient summary prepared by the device (500) during pre-consultation in cases where the patient makes some new revelations or corrections, or as instructed by the doctor. If the patient (601) adds further information about his/her condition while discussing with the doctor (602), the device (500) further modifies the previously prepared patient medical condition summary.
4. Taking notes of the instructions (703) as dictated by the doctor (602), if any. The doctor (602) may directly interact with the device (500) to give notes about the patient's condition or treatment notes or anything else. The device (500) converts those instructions as well to thought representations.
5. Preparing a final consultation summary (705), along with a patent treatment advice as instructed by the doctor. Post consultation, the device (500) prepares a comprehensive consultation summary.
6. Presenting the final summary (705) to the doctor (602) for his/her review (704) and making changes, if any, as instructed by the doctor (602).

7. Printing the patient treatment advice to be given to the patient (601).
8. Sharing (706) the final medical record with an external Electronic Medical Records System/Hospital Management System (707) connected with the device (500).
9. And, archiving the information and deleting it from its memory.

However, the passive listening of the device (500) during the patient-doctor consultation may not follow the exact sequence as explained above. The sequences may vary on case-to-case basis and/or with respect to situations.

The disclosed system (100) and device (500) are of considerable assistance to healthcare professionals or professionals in other domains.

It will be apparent to a person skilled in the art that the above description is for illustrative purposes only and should not be considered as limiting. Various modifications, additions, alterations and improvements without deviating from the spirit and the scope of the disclosure may be made by a person skilled in the art. Such modifications, additions, alterations and improvements should be construed as being within the scope of this disclosure.

LIST OF REFERENCE NUMERALS

100—BISLU System
101—First Module
1011—First Unit
1012—Second Unit
102—Buffer Module
103—Second Module
104—Third Module
105—Fourth Module
106—Fifth Module
107—Sixth Module
108—First Knowledge Base
109—Second Knowledge Base
110—One or More Microphones
111—Seventh Module
112—Eighth Module
113—Third Knowledge Base
114—Ninth Module
201—Third Unit
2011—Sliding Window
202—Fourth Unit
203—Fifth Unit
204—Sixth Unit
205—Sequence of Phonetics-Based Words
206—One or More Feedback from the Other Modules (103, 105, 106)
207—Status signal to the Second Module
301—Seventh Unit
302—Eighth Unit
303—Ninth Unit
304—Sequence of Thought Representations
305—One or More Feedback from the Other Modules (103, 106)
306—Status Signal to the Second Module
307—Entity Possibility Buffer Unit
401—Tenth Unit
402—Eleventh Unit
403—Twelfth Unit
404—Instance Blog of Stories from the Entire Conversation as Thought Representation.
405—One or More Feedback from the Other Modules (103)
406—Status Signal to the Second Module
407—Entity De-Referencing Unit
500—A Device for Implementing the BISLU System
501—At Least One Central Processing Unit
502—At Least One Input Unit
503—One or More Health Care Devices or a Network
504—Display Unit
505—At least One Microphone
506—At least One Speaker
507—At least One Camera
508—One or More Supplementary Processing Units
601—Patient
602—Doctor
603—Two-way Audio and Display-type Conversation/interface between 500 and 601.
604—Collecting Clinical Vital Data from the Patient by the Device
605—Patient Summary Shown to Patient.
606—605 after Correction by Patient.
607—Preparing a Doctor-specific Summary and Forwarding to the Doctor
701—Patient-Doctor Conversation
702—Listening to a Patient-Doctor Conversation by the Device
703—Taking Notes of the Doctor's Instructions to the Device
704—Doctor Reviewing and Correcting Final Consultation Summary
705—Final Consultation Summary created by the Device and Corrected by Doctor.
706—Sharing the Medical Record with an External System Connected with the Device
707—External System

We claim:

1. A brain-inspired spoken language understanding system, comprising:
a non-volatile computer readable storage media with a plurality of software modules stored thereon, the plurality of software modules including a first module, a second module, a third module, a fourth module, a fifth module, a sixth module, a seventh module, an eighth module, a ninth module, and a buffer module, wherein:
the first module converts a voice input received through one or more microphones into phoneme sequences, said first module comprising: a first unit that converts the voice input received into spectrograms, and a second unit that converts the spectrograms into phonemes, with pause time between the phonemes, if applicable;
the buffer module stores the phoneme sequences until the phoneme sequences are clustered into a first storage as one or more meaningful thought representations;
the second module monitors reasoning, disambiguation, and prioritization of the system, in addition to controlling the system;
the seventh module comprises: at least one sensor that captures at least one non-verbal signal from a conversation, and a pre-processing unit that pre-processes the at least one non-verbal signal;
the eighth module is configured to classify and transform the at least one non-verbal signal into at least one symbol, and create at least one time-synchronized non-verbal object by permuting and matching the at least one symbol against a third knowledge base, said third knowledge base providing a look-up for non-verbal symbols into known complex objects;

the ninth module transmits the at least one time-synchronized non-verbal object, along with a timestamp, to the third module;

the third module converts the phoneme sequences and at least one time-synchronized non-verbal object into sequences of phonetics-based words;

the fourth module converts the phonetics-based words into sequences of thought representations in the form of concepts based on the phonetics-based words, utilizing a first knowledge base, wherein the first knowledge base comprises words or vocabularies or lingo related to clinical concepts and/or limited worldly knowledge concepts;

the fifth module fine-tunes the thought representations received from the fourth module by: merging two or more thought representations, inferring new thought representations, correcting the thought representations, and/or filling one or more missing information in the thought representations, utilizing the first knowledge base and a second knowledge base, wherein the second knowledge base comprises a thought representation semantic network;

the sixth module stores an instance of conversation as thought representations in the form of one or more connected stories, with said third module, said fourth module, and said fifth module interacting with each other, and with the system running sequence possibilities throughout said third module, said fourth module, and said fifth module with feedback coming from said fifth module to said fourth module and from said fourth and fifth modules to said third module; and at least one central processing unit is communicatively coupled to the non-volatile computer readable storage media and configured to execute the plurality of software modules.

2. The brain-inspired spoken language understanding system as claimed in claim 1, wherein the third module comprises: a third unit that collects phonemes from the buffer module and uses sliding dynamic width window technique over these phonemes to create a sequence of best possible phonetics-based words, said third unit receiving one or more feedback to decide whether the phonetics-based words are meaningful or not, and sending status signals to the second module after the completion of a task; a fourth unit that receives the phoneme sequences from the third unit and converts the phoneme sequences into phonetics-based words; a fifth unit that receives the sequence of phonetics-based words identified by the third unit and refines the phonetics-based words; and a sixth unit, which is a phoneme similarity matrix that resolves conflicting words by using similar sounding phonemes.

3. The brain-inspired spoken language understanding system as claimed in claim 1, wherein the fourth module comprises: a seventh unit that takes sequences of phonetics-based words as input, and, fetches possible concepts/entities from a single phonetics-based word or a group of phonetics-based words, utilizing with the first knowledge base, with output concepts being sent to an entity possibility buffer unit; an eighth unit that holds sequences of phonetics-based words since a previous completion of a thought representation and outputs: expected phonetics-based words or concept type for the given sequence of previous phonetics-based words and thought representation for sequence of phonetics-based words; and a ninth unit that identifies the best possible and meaningful thought representations by reasoning the phonetics-based words in the entity possibility buffer unit with all the thought representations obtained since a previously completed thought representation process, said ninth unit receiving one or more feedback to decide whether the thought representations are meaningful or not, and sending status signal to the second module during a current task or after completion of the current task.

4. The brain-inspired spoken language understanding system as claimed in claim 1, wherein the fifth module comprises: an entity de-referencing (EDR) unit that receives incoming thought representation sequences from the fourth module, keeps track of all entities mentioned throughout the conversation, and updates the incoming thought representation sequences with well-specified entities; a tenth unit that checks whether the thought representations are well-connected and switching between their contexts is meaningful, utilizing the first knowledge base; an eleventh unit that explores all possible thought representation context connectivity; and a twelfth unit that fine-tunes the thought representations received from the fourth module by: merging two or more thought representations, inferring new thought representations, correcting the thought representations, and/or filling one or more missing information in previous thought representations, utilizing the second knowledge base, and creates a story based on the thought representation sequence, said twelfth unit receiving one or more feedback from the second module to decide whether to process further or stop processing, and sending status signal to the second module during a current task or after the completion of the current task.

5. The brain-inspired spoken language understanding system as claimed in claim 1, wherein the first knowledge base is based on Unified Medical Language System.

6. The brain-inspired spoken language understanding system as claimed in claim 1, wherein the first knowledge base and the second knowledge base are configured to have prioritized access based on frequency and recentness of access.

7. The brain-inspired spoken language understanding system as claimed in claim 2, wherein the fourth unit is configured as a predictive memory.

8. The brain-inspired spoken language understanding system as claimed in claim 3, wherein the eighth unit is configured as a predictive memory.

9. The brain-inspired spoken language understanding system as claimed in claim 4, wherein the eleventh unit is configured as a predictive memory.

10. The brain-inspired spoken language understanding system as claimed in claim 4, wherein the tenth unit detects context-switching anomalies and thought-specific anomalies.

* * * * *